United States Patent [19]

Ramsay

[11] Patent Number: 4,577,755
[45] Date of Patent: Mar. 25, 1986

[54] SURGICAL INSTRUMENT TRAY

[76] Inventor: Mitchell Ramsay, 5948 S. Suwannee Cir., Salt Lake City, Utah 84107

[21] Appl. No.: 582,385

[22] Filed: Feb. 22, 1984

[51] Int. Cl.⁴ ............................................... B65D 83/10
[52] U.S. Cl. ..................................... 206/370; 206/560; 34/237; 211/88
[58] Field of Search .................. 34/237, 238; 206/560, 206/557, 370; 211/88

[56] References Cited

U.S. PATENT DOCUMENTS

| | | |
|---|---|---|
| 27,237 | 2/1860 | Smith ..................................... 34/237 |
| 192,109 | 6/1877 | Brower et al. . |
| 732,089 | 6/1903 | Lenzen ................................. 206/560 |
| 1,282,094 | 10/1918 | Linder . |
| 1,783,453 | 12/1930 | Reisert ................................. 206/557 |
| 2,349,391 | 5/1944 | Usoskin ................................. 211/88 |
| 2,800,998 | 7/1957 | Holmquist ........................... 206/557 |
| 2,903,129 | 9/1959 | Anderson, III . |
| 3,868,016 | 2/1975 | Szpur et al. . |
| 3,925,014 | 12/1975 | Langdon . |
| 4,043,754 | 8/1977 | Sklar . |
| 4,135,868 | 1/1979 | Schainholz . |
| 4,229,420 | 10/1980 | Smith . |
| 4,342,391 | 8/1982 | Schainholz ......................... 206/459 |

FOREIGN PATENT DOCUMENTS 523662  11/1976  U.S.S.R. ................................ 34/237

*Primary Examiner*—Joseph Man-Fu Moy
*Attorney, Agent, or Firm*—Trask & Britt

[57] ABSTRACT

A surgical instrument tray has a base with a raised portion to support lever members of ring-handled surgical instruments. The base is formed to have an end portion angulating away from the base with slots formed therein sized to receive the ring handles attached to the lever members of the surgical instruments to hold the instruments in an upstanding manner. Apertures are positioned in opposite side members proximate the raised portion through which retaining members are positioned to hold the surgical instruments in the tray and to hold the working member portion of the surgical instrument separate to facilitate sterilization. The retaining members are arcuate in shape in order to apply a spring-like force to retain selectively surgical instruments in the tray and to selectively hold the lever member of the instrument apart so that the working members of the surgical instrument are separate.

17 Claims, 1 Drawing Figure

SURGICAL INSTRUMENT TRAY

BACKGROUND OF THE INVENTION

1. Field:

This invention relates to surgical instrument trays. More particularly, this invention discloses an improved surgical instrument tray to use, store, transport, and sterilize surgical instruments.

2. State of the Art:

Modern day surgery involves the use of a wide variety of different surgical instruments, including retractors and other kinds of clamps. Many of the instruments are of the scissors type and have lever members which connect through a pivot to working members. The instruments are typically of various types and designs to effect a variety of surgical purposes in a medical or hospital operating room environment. The lever members typically have handles to facilitate opening and closing by the user's fingers.

It is often desirable to have surgical instruments organized or collected in trays or other receptacles in a particular sequence or order for use in specific surgical procedures such as an appendectomy or the like. Further, it is frequently desirable to sterilize batches or quantities of surgical instruments in an autoclave or other device used for sterilizing surgical instruments. In addition, applicant understands that it is typical to periodically inventory and to otherwise maintain close control of surgical instruments.

A variety of devices exist for storing and controlling surgical instruments. For example, U.S. Pat. No. 4,229,420 (Smith) discloses a surgical instrument rack having two sections or members which may be separated to load and unload the rack and which may be latched together to secure a number of ring-handled surgical instruments. This device is difficult to handle and place in an autoclave, is complex in structure, and does not protect the working members of the instruments from accidental touching or bumping. U.S. Pat. No. 3,925,014 (Langdon) discloses a wire rack type device for storing and supporting surgical instruments. This device employs special clamps to hold and group instruments and does not lend itself to easy use in an autoclave. Further, the working members are not protected from touching or bumping.

U.S. Pat. No. 2,903,129 (Anderson III) discloses a device in which instruments are not secured so that the device, with instruments in place, cannot be placed in a variety of positions in an autoclave.

There appears to be a need for a simple surgical instrument tray which is useful for using, storing, inventorying, sterlizing, transporting, and dispensing surgical instruments in an organized manner. The tray should be inexpensive, sterilizable and susceptible to easy use proximate the operating site in an operating room environment.

SUMMARY OF THE INVENTION

A surgical instrument tray includes a base with first and second opposite side members affixed thereto and extending away therefrom to form an area therebetween for the placement of surgical instruments. Retaining members extend between the side members and are removably secured thereto by securing means. In one embodiment, the side members have a plurality of apertures formed therein to receive the retaining members. The retaining members are sized to extend through an aperture in one side member to and through an aperture in the other side member. The retaining members are removably and selectively positioned through the apertures to retain the surgical instruments in the area.

The retaining members are formed to be arcuate in shape and made of a material so that when positioned through selected apertures, a spring pressure is exerted against the surgical instruments in the area. In another embodiment, the base member is formed to have a section raised in the direction of the side members. The apertures are formed in the side members proximate the raised portion.

The base member preferably has an end portion which extends away from the base in the direction of the side members. The end section is formed with handle retaining means sized to receive the handle portion of surgical instruments.

In another embodiment, the tray is formed specifically for holding surgical instruments of the type having ring-like handles on the ends of lever members connected through a pivot to working members. The base member has a first section sized in length to receive the working member portion of the instruments. The raised portion is connected to the first section and sized in length to receive the lever member portion of the instruments. An end section is connected to the raised portion and extends angularly away therefrom. The end section has a plurality of elongated slots formed and extending angularly away from the raised section which are sized to receive the ring-like handles of the surgical instruments. Side members are affixed to the base member and have a plurality of apertures formed therein proximate the raised section of the base member. The retaining member is sized to extend through an aperture in one side member to and through an aperture in another side member. The retaining member is removably and selectively positionable through the aperture to retain a selected surgical instrument in the tray. Preferably, the retaining member is positioned through selected apertures to retain one of the lever members of selected instruments snugly against the raised portion. A second retaining member is positioned through selected apertures to urge the other lever member of selected instruments away from the base.

In another embodiment, other side members are attached to the base and to the side members to form a box-like structure. The tray is preferably made of an autoclavable material. In an alternate and preferred environment, the end section of the base angulates upwardly therefrom at an angle from about 15 degrees to about 80 degrees. Preferably, the raised section is elevated above the first section a height substantially the width of the ring-like handle attached to the lever member of a ring-like surgical instrument.

BRIEF DESCRIPTION OF THE DRAWING

The drawing illustrates the best mode presently contemplated for the carrying out of the invention. The drawing is a perspective three-dimensional view of a surgical instrument tray of the instant invention with a cut-away portion.

DESCRIPTION OF THE ILLUSTRATED EMBODIMENTS

Figure 1:
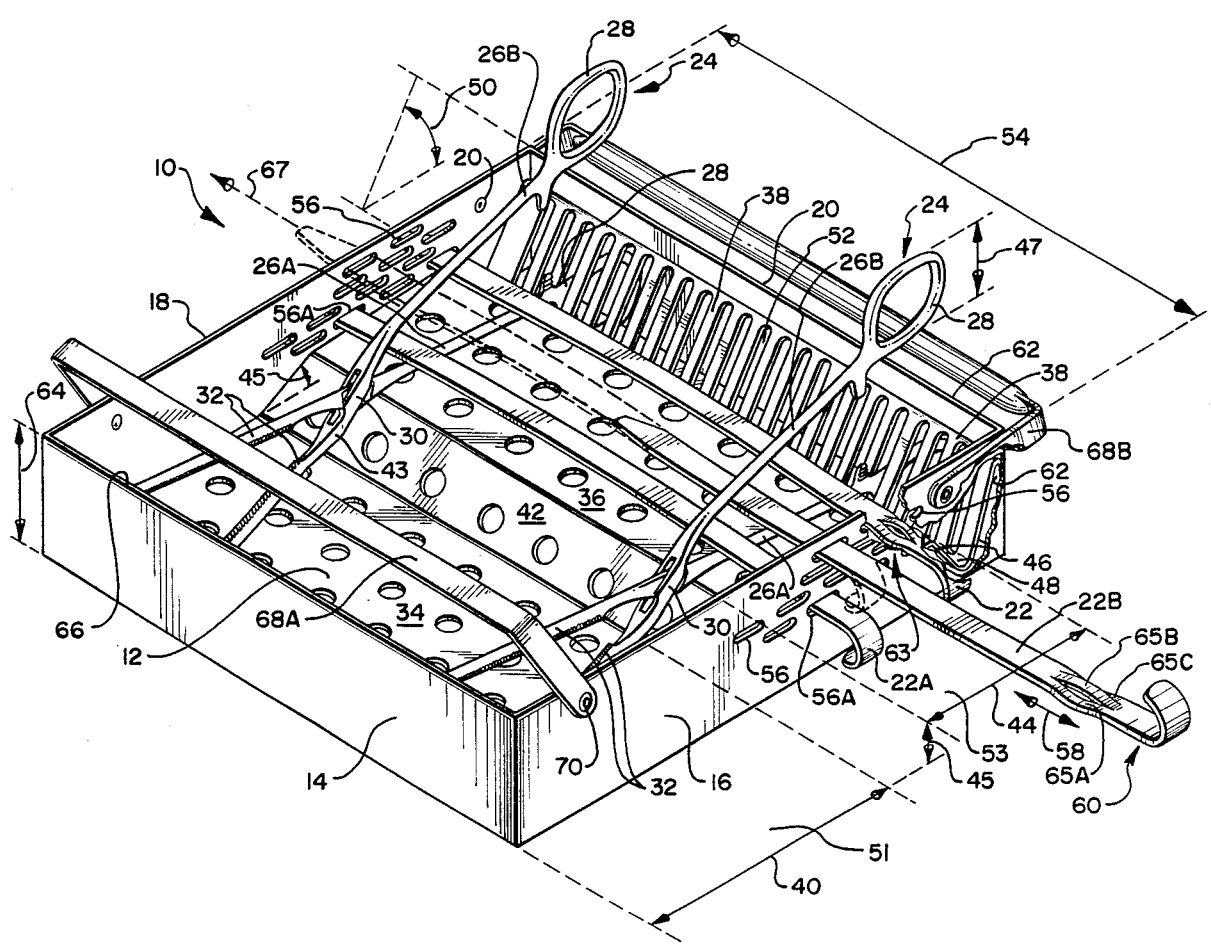

In the drawing, the numeral 10 generally denotes a surgical instrument tray of the instant invention. The tray 10 has a base 12 with a first side member 16, a second side member 18, a third side member 14, and a fourth side member 20. As illustrated, the side members and base are assembled preferably to form a box-like structure.

The tray 10 is formed and sized to receive a plurality of surgical instruments which are retained therein by retaining members 22 as more fully discussed hereinafter. The tray 10 is particularly suited for retaining surgical instruments 24 which, as shown, are of the type which have lever members 26 with ring-like handles 28 affixed to the ends thereof. The lever members 26 are connected through a pivot 30 in a scissors-like fashion to working members 32.

The base 12 is formed to have a first section 34, a raised section 36, and an end section 38. The first section is sized in length 40 to receive the working members 32 of the surgical instruments 24. The raised section 36 is connected to the first section 34, as here illustrated, by an inclined section 42. Other means of connecting the first section 34 to the raised section 36 may be used as desired so long as such means does not interfere with the shoulders 43 of the instruments 24 or with similar mechanical portions of surgical instruments which are of the type to be positioned in the tray 10 and which are not here illustrated.

The raised section 36 of the base 12 is sized in length 44 to receive one of the lever members 26A of the instrument 24. As can be seen, the length 44 is less than the overall length of the lever member 26A in order to accommodate instruments of different sizes while at the same time providing sufficient stability to the instruments for storage, sterilization, and transport in and about the operating room environment. The raised section 36 is elevated above the first section in height 45 slightly more than the width 47 of the ring handles or other handles of surgical instruments to be placed in the tray 10.

The end section 38 is connected to the raised section 36. As here illustrated, the end section 38 is connected via an inclined surface 46 which, in effect, forms a type of well or trough 48. The end section 38 angulates upwardly with respect to the base 12 at an angle 50 which may be from approximately 15 degrees to about 80 degrees with respect to either the plane 51 of the first section 34 or the substantially parallel plane 53 of the raised section 36. The angle 50 is preferably selected to be from about 45 degrees to about 60 degrees to facilitate ease in inserting and extracting the handles of instruments such at those illustrated 24.

The handles of the instruments are positioned through elongated slots 52 which are formed, as here illustrated, in a side-by-side relationship along the width 54 of the end section 38. The elongated slots 52 extend in the direction away from the base 12 in an upward direction so that surgical instruments may be placed in an upstanding fashion as illustrated. The slots 52 are means to removably hold the handles of surgical instruments such as the ring-handled instruments 24 illustrated. However, other means may be used to accept handles of instruments which are to be placed in the tray 10 and which are not here illustrated. However, the other means should preferably provide for drop-in/pull-out placement removal similar to that shown for the ring-handled instruments 24.

The first and second side members 16 and 18 are formed with a plurality of apertures 56 which are preferably positioned proximate the raised section of 36. A retaining member 22 is positioned through an aperture 56 in the first side member 16 through the surgical instrument area between the first side member 16 and the second side member 18 to and through an aperture 56 in the second side member 18. For the instruments 24 here illustrated, the lever members 26A are retained against the surface of the raised section 36. The retaining member 22 is preferably arcuate in shape so that when positioned through apertures 56, the retaining member 22 exerts a spring-like pressure against either or both of the lever members 26A or 26B of the surgical instruments 24.

The slots 56 as here shown are elongated to receive retaining members which are preferably rectilinear in a cross section taken normal to the length 58 of the retaining member 22. The retaining member 22 also may have a handle means here shown to be a portion 60 unitarily formed as a part of the member 22.

The retaining member 22 preferably is a flat, elongated metal strap. However, it may be of any particular material desired by the user so long as it is acceptable for use in an autoclave and has sufficient structural strength to hold the instruments in place. Also, the member 22 may be formed to be eliptical or circular in cross section or in another shape as desired so long as the member provides the necessary retaining capability. Of course, the apertures 56 are shaped and sized to snugly and slidably accept the retaining member 22. The flatlike (rectilinear in cross section) form of the member 22 is preferred in that it provides increased retaining stability to one or more surgical instruments positioned within the tray 10 during transport or movement in and about the operating room environment.

It should also be noted that a plurality of retaining members may be used. A first retaining member 22A may be positioned in appropriate apertures 56A to retain the lever member 26A of one or more instruments snugly against the raised section 36 of the base 12. In some cases, the use of one retaining member is sufficient in that it will simultaneously hold the lever member 26A against the raised surface 36 and the other lever member 26B of the same instrument outward so that the working members 32 of the surgical instrument are spaced apart to provide open surfaces for full or more complete sterilization when placed in an autoclave or similar sterilizing aparatus. Alternatively, another retaining member 22B may be positioned through selected apertures 56 to urge the other lever member 26B outward to retain the working members spaced apart and to simultaneously hold the surgical instrument snugly in place and to avoid disruption in the event the ring handles 28 or lever members 26 are bumped or touched during movement or handling of the tray 10. It should also be noted that the retaining members 22 are formed to be arcuate in shape. That is, the members 22 are bowed along their length 58 as illustrated. The arcuate shape is preferably oriented downward toward the surfaces 34 or 36 convex as to the surfaces 34, 36 for the first retaining member 22A to urge the lever member 26A downward toward the surfaces 34, 36. Another retaining member 22B may be oriented preferably with the arcuate shape in an upward direction concave as to the surface 34, 36 in order to urge the other lever member 26B of an instrument outwardly. Additional retaining members 22 may be used as desired. All retaining members 22 are desirably removed prior to use of the instruments in a surgical procedure.

The apertures 56 are formed in a matrix in order to accommodate a mixture of different instruments, including those which may not have a scissor-type configuration and including those in which the lever members are closed for the working members to be open. The apertures 56 in the first side member 16 are preferably in registration with the apertures 56 in the second side member 18 so that a retaining member 22 may be inserted through the first side member 16 and moved in a substantially straight line to and through a corresponding aperture 56 in the second side member 18. A retaining member 22 may be inserted through nonregistered aperatures 56 to accommodate different types or sizes of instruments.

The retaining members 22 preferably have securing means 63 associated therewith to retain them in the apertures when there is no force to hold them securely in place as, for example, when there are no or only a few instruments in the tray 10. The securing means 63 is shown to be a plurality of leaf members 65A, B and C unitarily formed as part of the retaining member 22. The leaf members 65 are displaced away from the retaining member 22 and are spring like. In use, the retaining member 22 is inserted through the apertures 56 until the securing means 63 passes through the aperture. The handle 60 prevents the retaining member 22 from passing entirely through the aperture 56 in an inward direction 67; and the securing means 63 inhibits movement in an outward direction (opposite to inward). The user need only apply force to the handle means 60 to overcome the spring force of the leaf members 65 to insert or remove the retaining member 22.

It should also be noted that the end portion 38 of the base 12 extends to an upper edge 62 to form a space 62 to receive the handle of an instrument which, as here shown, is the ring handle 28 of the lever member 26 of the surgical instrument 24.

As noted hereinbefore, the tray 10 is preferably formed to be a box-like structure. The sides 14, 16, 18, and 20 are sized in height 64 so that substantially all of the working members 32 of instruments, such as the instruments 24 shown, are retained below or within the upper edge 66 of the proximate side members and substantially within the area formed by the side members. The base 12 and side members 14, 16, 18, and 20 are formed of an autoclavable material which may be plastic but is preferably stainless steel because it is presently most suited to the medical operating room environment. Stainless steel is accepted as a sterilizable material. Also, a tray 10 made from stainless steel is sturdy and heavy to have enough weight or inertia so that it is not easily or readily moved (e.g., knocked off a table) by, for example, an accidental bump. The side members 14, 16, 18, and 20 are formed to be flat surfaces so that the tray 10 may be positioned in an autoclave or other sterilizing apparatus on any one of its side surfaces as well as on its base. Further, the box-like structure provides for stability when positioned on a table or stand proximate a patient for the dispensing of instruments.

The tray 10 preferably has handles 68 affixed thereto to facilitate transport. The handles 68 are rotatable about pivots 70 and are mounted so they may be moved out of the way to facilitate placement in an autoclave and to permit the placement and removal of instruments in the tray 10. The pivot points 70 are selected and the handles 68 are sized so that handles may fold over the edge 66 and edge 62 of the third and fourth side members as shown. The handle 68A is shown as formed from flat bar or strap material. Handle 68B is shown to be tubular for that portion which is held in the hands. Handle 68B is preferred since it is regarded as more comfortable to use.

The base 12 is preferably formed to permit sterilizing material to flow therethrough. A plurality of holes or apertures may be formed therein. In the alternative, a screen mesh material may be used for all or a selected portion of the base 12. As hereinbefore noted, the retaining members 22 are made of a rigid material which is preferably stainless steel.

It is to be understood that the embodiments of the invention herein described are merely illustrative of the application of the principles of the invention. Reference herein to details of the illustrated embodiment is not intended to limit the scope of the claims which themselves recite those features regarded as essential to the invention.

I claim:

1. A surgical instrument tray comprising:
   a base member;
   first and second opposite side members each affixed to said base and extending away therefrom to form an area therebetween for the placement of surgical instruments, each of said instruments having movable lever members which are movable with respect to one another about a pivot;
   a plurality of apertures formed in each of the side members wherein some of the apertures in the first side member are substantially opposite some of the apertures in the second side member;
   retaining members each sized to extend through an aperture in said first side member to and through an aperture in said second side member, said retaining members being removably and selectively positionable through said apertures and against said movable lever members of said surgical instrument to retain said surgical instruments with said movable lever members in a predetermined orientation within said area.

2. The tray of claim 1 wherein at least one of said retaining members is formed to be arcuate in shape and made of a material selected so that when positioned through said selected apertures, a spring pressure is exerted against selected surgical instruments in said area.

3. The tray of claim 1 wherein said base member is formed to have a section raised in the direction of said first and second side members and therebetween, wherein said apertures in said side members are proximate said raised section, and wherein some of the apertures in the first side member are in registration with some of the apertures in the second side member.

4. The tray of claim 1 wherein said base member has an end section which extends away from said base in the direction of said side members, said end section being formed with handle retaining means sized to receive the handles of selected surgical instruments and retain the instruments in a substantially up-standing orientation with respect to said base member.

5. The tray of claim 1 wherein said side members are substantially normal to said base member.

6. A tray for surgical instruments of the type having ring-like handles on the ends of movable lever members which are connected through a pivot to working members, said lever members being positionable in two orientations, a first orientation wherein said working members are in contact with one another and a second orientation wherein said working members are out of contact with one another, said tray being comprised of:

a base member having
- a first section sized in length to receive the working members of said instruments,
- a raised section connected to said first section sized in length to receive the lever members of said instruments, and
- an end section connected to said raised section and extending angularly away therefrom, said end section having a plurality of elongated slots formed therein extending angularly away from said raised section and sized to receive the ring-like handles of said instruments;

first and second side members connected to said base member to extend away therefrom to form an area therebetween containing said raised section and said end section;

a plurality of apertures formed in each of said first and second side members proximate the raised section of said base member; and a retaining member sized to extend through an aperture in said first side member to and through an aperture in said second side member, said retaining member being removably and selectively positionable through said apertures and against said lever members to retain said lever members of said surgical instruments in said second orientation within said tray.

7. The tray of claim 6 wherein said retaining member is formed to be arcuate in shape and made of a material selected so that when positioned through said selected apertures, a spring pressure is exerted against the lever members of selected surgical instruments in said area to retain said instruments therein with their working members separated.

8. The tray of claim 7 wherein a first retaining member is positioned through selected apertures to retain one of the lever members of the selected instruments snugly against said raised portion and a second retaining member is positioned through selected apertures to urge the other lever member of the instrument away from the base.

9. The tray of claim 8 wherein said apertures in the first side member are substantially in registration with the apertures in the second side member.

10. The tray of claim 8 wherein said base, side members, and retaining member are made of an autoclavable material.

11. The tray of claim 8 wherein said base raised section is substantially flat and wherein said end section angulates upwardly at an angle from about 15 degrees to about 80 degrees from said base.

12. The tray of claim 8 wherein said base is formed for the passage of autoclaving material therethrough.

13. The tray of claim 8 wherein the raised section is elevated above the first section a height substantially the width of a ring-like handle of an instrument.

14. The tray of claim 8 including a third side member and a fourth side member selectively connected to said base and to said first and second side members to form a box-like structure.

15. The tray of claim 14 having handle means secured to selected side members.

16. The tray of claim 14 wherein said base member and side members are sized so that, with surgical instruments positioned thereon, said tray is positionable within a surgical instrument autoclave, and so that the working members of said instruments are substantially below the upper edge of the side members proximate thereto.

17. The tray of claim 7 wherein said retaining member has securing means associated therewith to hold said retaining member in place when inserted in said selected apertures.

* * * * *